United States Patent [19]

Brooker et al.

[11] 4,378,367
[45] Mar. 29, 1983

[54] COMPOSITIONS CONTAINING 2,2-DIMETHYL-1,3-BENZODIOXOL-4-YL N-METHYLCARBAMATE FOR TREATING SEEDS

[75] Inventors: Peter J. Brooker, Saffron Walden; Quinton A. Geering, Little Eversden, both of England

[73] Assignee: FBC Limited, Cambridge, England

[21] Appl. No.: 14,159

[22] Filed: Feb. 22, 1979

Related U.S. Application Data

[63] Continuation of Ser. No. 906,569, May 16, 1978, abandoned, which is a continuation-in-part of Ser. No. 662,083, Feb. 27, 1976, abandoned.

[51] Int. Cl.³ .................... A01N 43/16; A01N 43/36
[52] U.S. Cl. .................................. 424/274; 424/282; 47/57.6; 47/DIG. 9
[58] Field of Search ................. 424/282, 274; 47/57.6, 47/DIG. 9

[56] References Cited

U.S. PATENT DOCUMENTS

| | | | |
|---|---|---|---|
| 2,845,453 | 7/1958 | Brooks | 260/500 |
| 3,336,129 | 8/1967 | Herrett et al. | 71/92 |
| 3,948,952 | 4/1976 | Gates et al. | 424/282 |
| 4,056,625 | 11/1977 | Gates et al. | 424/282 |

FOREIGN PATENT DOCUMENTS

1220056  1/1971  United Kingdom ............... 424/282

OTHER PUBLICATIONS

Kirk–Othmer, Encyclopedia of Chemical Technology, Second Edition, Vol. 11, p. 713 (1966).
Frear, Pesticide Handbook, pp. 301–302 (1964).

*Primary Examiner*—Allen J. Robinson
*Attorney, Agent, or Firm*—Wenderoth, Lind & Ponack

[57] ABSTRACT

Seeds dressed with 2,2-dimethyl-1,3-benzodioxol-4-yl N-methylcarbamate exhibit excellent resistance to insecticidal attack.

7 Claims, No Drawings

COMPOSITIONS CONTAINING 2,2-DIMETHYL-1,3-BENZODIOXOL-4-YL N-METHYLCARBAMATE FOR TREATING SEEDS

This is a continuation of application Ser. No. 906,569, filed May 16, 1978, now abandoned which in turn is a continuation-in-part of Ser. No. 662,083, filed Feb. 27, 1976, now abandoned.

This invention concerns dressed seed.

As shown in the Pesticide Handbook, 16th edition, by Frear, published by College Science Publishers, State College, Pennsylvania, crop seeds have hitherto been treated with certain insecticidally-active or fungicidally-active materials in order to protect them from insect or fungal attack.

Since such attacks occur predominantly in the soil, leading to decreased emergence and yield of the crop, it is clear that any material used to treat seeds should be stable in the soil if it is to remain effective for a sufficient time to prevent or reduce such effects. As is well-recognised, however, the soil represents a very hostile environment for pesticides, there being many factors which exist to reduce their effectiveness and persistence therein. These include the continuous aqueous phase, the pH, the effects of the heat and light of the sun, the action of soil micro-organisms and the reaction with, or sorption on, the organic and silicaceous colloids of the soil. Consequently, only pesticides of extremely high stability and persistence have been able to be employed. In fact, as is clear from the Pesticide Handbook referred to above, the only class of insecticides which has been able to be so used comprises organochlorine insecticides, e.g. BHC, methoxychlor and heptachlor.

However, organochlorine compounds are highly toxic to animals and birds, and this combined with their extreme persistence, has made their use undesirable and frequently unacceptable. Unfortunately, hitherto, there has been no reasonable alternative to their use, in spite of the undeniable need for such an alternative, and in spite of the existence of many other known classes of insecticide.

Carbamate insecticides have been known and used for some time for certain purposes, but are generally of low stability and break down readily after application, giving only short duration of activity. As a consequence, carbamate insecticides have been thought to be unsuitable for use as seed treatments since the duration of activity in the hostile environment which the soil provides would be too short to provide any useful benefit.

We have now found that a particular carbamate insecticide may be employed as a seed treatment which is of satisfactory duration of activity, low toxicity to animals and birds, and surprisingly high insecticidal activity when compared with known insecticides in such applications.

Accordingly, in one aspect, this invention provides seed dressed with from 0.1 g to 28 g, preferably with from 0.1 to 18 g, and more preferably with from 0.25 g to 10 g, of 2,2-dimethyl-1,3-benzodioxol-4-yl N-methylcarbamate (common name bendiocarb) per kg of seed.

By the term 'dressed' as used herein is meant that the seed is either in intimate admixture with the 2,2-dimethyl-1,3-benzodioxol-4-yl N-methylcarbamate or is coated therewith. Most desirably, the seed is dressed with the carbamate by dusting with a dry composition, containing the active ingredient, by admixture with a slurry containing it, by a conventional spray-coating technique in which the carbamate is dissolved or dispersed in a volatile solvent which is sprayed over the seed and allowed to evaporate, or by a conventional pelletising process in which the carbamate is mixed with a solid carrier, e.g. a clay or woodmeal, and the seed is coated with the mixture. Naturally, the technique chosen will to some extent depend upon the seed to be dressed. Seeds which may be dressed in accordance with the invention include, merely as examples, rape, vegetables, notably brassicas, onions and beans (for example soya beans), cereals, notably wheat, barley, oats and maize, and root crops, especially sugar beet. The dressing treatment applied to each will normally depend upon conventional treatment for such seed. Thus, sugar beet seed, which is often pelleted, will normally be dressed in accordance with the invention by pelletisation. Cereals, however, which are not normally pelleted, will preferably be dressed in accordance with the invention by, for example, dusting or spray coating. Dressing of larger seeds, e.g. those of beans, is desirably facilitated by means of a 'sticker', e.g. carboxymethylcellulose, to enable the active ingredient to adhere thereto.

The dressed seed of the present invention shows surprisingly high seedling emergence and establishment in the presence of insect pests, and it appears moreover that the carbamate may surprisingly be absorbed systemically by the seedling to provide post-emergent resistance to insect attack.

In another aspect, this invention provides a process wherein seed is dressed with from 0.1 to 28 g, preferably with from 0.1 to 18 g, and most desirably with from 0.25 to 10 g, of 2,2-dimethyl-1,3-benzodioxol-4-yl N-methylcarbamate per kg of seed.

Insects against which the present dressed seeds are effective include coleoptera and diptera, for example wireworms (Agriotes spp), pygmy beetle (Atomaria), collembola and millipedes, symphilids and flea beetles (Chaetocnema Spp).

In another aspect therefore this invention provides a method of insect control in which seed dressed in accordance with the present invention is planted so as to give a concentration of carbamate per hectare of from 0.2 g to 400 g in a locus either infested with or liable to infestation by said insects. The concentration of carbamate per hectare naturally depends largely on the rate of planting of the seeds, and this varies with the chosen crop. Thus, for example, a preferred concentration of carbamate when sugar beet is the chosen seed is from 1–15 g per hectare, whereas if a cereal crop such as wheat is employed, the preferred rate may well be 200 g/hectare or more.

The seed may be dressed according to the present invention with mixtures of active ingredients which contain, in addition to the carbamate, other active insecticides or fungicides. Particularly useful for seed dressing are mixtures of the carbamate with fungicides, for example thiram (especially preferred), benzoquinox, captan or S-ethyl N-(3-dimethylaminopropyl) thiocarbamate or salts thereof, e.g. the hydrochloride, and this invention not only provides seed when dressed therewith, but also mixtures of the carbamate with the fungicides specifically named, which are synergistic.

The invention will now be further described, though only by way of illustration, in the following Examples.

EXAMPLE 1

Sugar beet seed was dressed in accordance with the present invention by pelletisation following the procedure of the Maribo process (Zucker, 26 (10), 533–540 (1973)). 2,2-Dimethyl-1,3-benzodioxol-4-yl N-methylcarbamate was incorporated into the pelletising composition to give a final concentration of 10 g per kilogram of naked seed.

EXAMPLE 2

Cabbage seed was dressed in accordance with the present invention as follows:

2 kg of cabbage seed was placed in a metal drum and 20 g of dressing of the following composition was added.

|  | % by weight |
|---|---|
| 2,2-dimethyl-1,3-benzodioxol-4-yl N—methylcarbamate | 2.5% |
| Attaclay | 15% |
| Risella oil 17 | 4% |
| Berkbond No 1 (a silicaceous filler) | 78.5% |

The sealed drum was rotated on horizontal rolls for 30 minutes to achieve even dressing of the seed.

EXAMPLE 3

Wheat was dressed in accordance with the present invention as follows:

10 kg of wheat was placed in a metal drum and 50 g of dressing of the following composition was added.

|  | % by weight |
|---|---|
| 2,2-dimethyl-1,3-benzodioxol-4-yl N—methylcarbamate | 10% |
| Attaclay | 15% |
| Risella oil 17 | 4% |
| Berkbond No 1 | 71% |

The sealed drum was rotated on horizontal rolls for 30 minutes to achieve even dressing of the wheat.

EXAMPLE 4

Eight sites were plated at equal rates (equivalent to about 3 kg of pellets or 100,000 seeds per hectare) with pelleted sugar beet seed. At each site, discrete areas were planted with control pellets containing no active ingredient, and with pellets containing a range of concentrations of bendiocarb, heptachlor (a commercially-available chlorinated hydrocarbon insecticide) and Carbofuran (a commercially-available carbamate insecticide). The results in plant establishment per meter were as follows:

|  | Compound grams a.i. per 100,000 seeds or per ha | Control 0 | Heptachlor 6.0 | Carbofuran 30.0 | Carbofuran 45.0 | Carbofuran 90.0 | Carbofuran 150.0 | Bendiocarb 3.0 | Bendiocarb 6.0 | Bendiocarb 12.0 |
|---|---|---|---|---|---|---|---|---|---|---|
| Site No | 1 | 0.44 | 2.76 | 7.88 | 8.29 | 8.18 | 8.03 | 5.34 | 7.19 | 7.36 |
|  | 2 | 3.27 | 4.87 | 5.33 | 5.92 | 6.14 | 5.62 | 5.37 | 5.85 | 5.84 |
|  | 3 | 7.08 | 7.41 | 7.07 | 7.17 | 6.68 | 6.36 | 6.88 | 7.33 | 7.19 |
|  | 4 | 2.78 | 6.45 | 6.87 | 7.43 | 6.83 | 5.68 | 7.01 | 6.37 | 7.13 |
|  | 5 | 0.46 | 2.07 | 5.49 | 6.24 | 6.13 | 6.20 | 4.13 | 5.63 | 5.87 |
|  | 6 | 6.72 | 6.98 | 6.75 | 7.15 | 7.04 | 6.68 | 6.71 | 7.02 | 7.31 |
|  | 7 | 1.49 | 2.87 | 3.57 | 2.52 | 3.73 | 3.30 | 2.39 | 2.38 | 3.13 |
|  | 8 | 6.94 | 7.20 | 7.08 | 7.44 | 6.95 | 6.91 | 7.02 | 7.10 | 7.17 |
|  | mean | 3.65 | 5.08 | 6.26 | 6.52 | 6.46 | 6.10 | 5.60 | 6.11 | 6.41 |
|  | % of control | 100 | 139 | 172 | 179 | 177 | 167 | 153 | 167 | 176 |

It can readily be seen from these results that bendiocarb gives substantially better plant establishment, i.e. substantially higher insect control than heptachlor at the same or lower application rates, and similar results to those obtained with carbofuran, but at application rates only a quarter of those required with carbofuran.

The difference in the rates needed to be applied for bendiocarb and carbofuran is shown not to be due to inherently different insecticidal activities by comparative laboratory tests, not in the soil, where the following results were obtained at equal rates of application. The results are expressed on a scale from 0 to 6 where higher numbers indicate greater activity, and 0 represents the fact that the compound killed less than 50% of the insects.

| Species | Carbofuran | Bendiocarb |
|---|---|---|
| Bean aphids | 6 | 6 |
| Red spider mite adults | 2 | 1 |
| Red spider mite eggs | 0 | 0 |
| Houseflies | 3 | 3 |
| Yellow fever mosquitos | 6 | 6 |
| Cabbage white butterfly larvae | 6 | 5 |
| Flour beetles | 0 | 2 |

From the above results of tests, which were on a representative range of insects, it can be seen that the activities of carbofuran and bendiocarb not in the soil were about equivalent.

EXAMPLE 5

Areas of a single site were sown at equal rates with intimate mixtures of sugar beet and, respectively, 2,2-dimethyl-1,3-benzodioxol-4-yl N-methylcarbamate (8 g/kg seed), the gamma isomer of 1,2,3,4,5,6-hexachlorocyclohexane (10 g/kg seed), and diethyl 3,5,6-trichloropyridyl phosphorothioate (10 g/kg seed). The establishment counts of plants per hectare for the three areas were respectively 67900, 46500 and 39600.

EXAMPLE 6

A seed dressing composition was prepared having the following constituents:

|  | % |
|---|---|
| 2,2-Dimethyl-1,3-benzodioxol-4-yl N—methylcarbamate (as 80% wettable powder) | 62.5 |

-continued

|  | % |
|---|---|
| Thiram technical | 30.5 |
| China clay | 7.0 |

This composition was prepared by intimately admixing the ground constituents, and was applied to sugar beet seed at a rate of 10 grams per kilogram of seed. The treated seed and a control batch of untreated seed were sown at the same rates at three sites, the results, expressed as the mean number of seedlings emerging per row meter, being as follows:

|  | Control | Dressed seed |
|---|---|---|
| Site A | 1.07 | 11.5 |
| Site B | 5.3 | 9.0 |
| Site C | 5.7 | 13.0 |

EXAMPLE 7

Compositions equivalent to those of Example 6 were prepared in which the Thiram technical was replaced by an equal amount of, respectively, benquinox, captan and S-ethyl N-(3-dimethylaminopropyl)thiocarbamate hydrochloride. Excellent results as regards emergence of seed dressed therewith were obtained.

We claim:

1. Seed dressed with from 0.1 g to 28 g of 2,2-dimethyl-1,3-benzodioxol-4-yl N-methylcarbamate per kg of seed.

2. Seed according to claim 1 dressed with from 0.1 to 18 g of 2,2-dimethyl-1,3-benzodioxol-4-yl N-methylcarbamate per kg of seed.

3. Seed according to claim 2 dressed with from 0.25 to 10 g of 2,2-dimethyl-1,3-benzodioxol-4-yl N-methylcarbamate per kg of seed.

4. Seed according to claim 1 which is vegetable, cereal or root crop seed.

5. Seed according to claim 4 which is seed of brassicas, onions, beans, wheat, barley, oats, maize or sugar beet.

6. Seed according to claim 1 which is also dressed with a fungicidally effective amount of at least one of tetramethylthiuram disulphide; 1,4-benzoquinone 1-benzoylhydrazone 4-oxime; 3a, 4,7,7a-tetrahydro-N-(trichloromethanesulphenyl) phthalimide or S-ethyl N-(3-dimethylaminopropyl)thiocarbamate or a salt thereof.

7. A method of protecting seeds from insects wherein a seed dressed with from 0.1 g to 28 g of 2,2-dimethyl-1,3-benzodioxole-4-yl N-methylcarbamate per kg of the seed is planted in a locus either infested or liable to infestation by said insects so as to give a concentration of 2,2-dimethyl-1,3-benzodioxole-4-yl-N-methylcarbamate therein of from 0.2 to 400 g per hectare.

* * * * *